(12) United States Patent
Nakamura et al.

(10) Patent No.: US 7,429,561 B2
(45) Date of Patent: Sep. 30, 2008

(54) METHOD FOR STIMULATING CELL GROWTH USING SPONGE PROTEIN HYDROLYSATES

(75) Inventors: Kenji Nakamura, Osaka (JP); Kouji Nakamura, Osaka (JP); Takeshi Okada, Osaka (JP); Tadao Miyake, Osaka (JP)

(73) Assignee: Kenji Nakamura and Koji Nakamura, Osaka (JP)

( * ) Notice: Subject to any disclaimer, the term of this patent is extended or adjusted under 35 U.S.C. 154(b) by 937 days.

(21) Appl. No.: 10/736,067

(22) Filed: Dec. 15, 2003

(65) Prior Publication Data

US 2004/0213753 A1    Oct. 28, 2004

Related U.S. Application Data

(63) Continuation of application No. 09/665,848, filed on Sep. 20, 2000, now abandoned.

(30) Foreign Application Priority Data

Apr. 4, 2000   (JP) ............................. 2000-102424

(51) Int. Cl.
*C07K 14/00* (2006.01)
*A61K 7/00* (2006.01)
*A61K 38/00* (2006.01)

(52) U.S. Cl. .............................. 514/2; 514/12; 530/300; 530/35; 424/9.1; 424/70.14

(58) Field of Classification Search ............... 424/70.14, 424/9.1; 530/300, 350; 514/2, 12
See application file for complete search history.

(56) References Cited

U.S. PATENT DOCUMENTS 5,646,246 A   7/1997  Pettit et al.
6,395,508 B1  5/2002  Shimamura et al.
6,399,105 B1  6/2002  Collin

FOREIGN PATENT DOCUMENTS

EP  1 062 873     12/2000
JP  2000-053696    2/2000

OTHER PUBLICATIONS

Tekman, et al. (DN 59:83368, HCAPLUS, abstract of Nature (1963), 200(4901), 77-8).
Saper, et al. (DN 52:52266, HCAPLUS, abstract of Nature (1958), 181, 285-6).
Theodoropoulas, et al., (DN 52: 12555, HCAPLUS, abstract of Chim. Chronika (1957), 22, 225-30).
Cmelik (DN 48: 56864, HCAPLUS, abstract of Hoppe-Seylers Z. Physiol. Chem. (1952), 289, 218-20).
Roche, et al., (DN 47: 4511, HCAPLUS, abstract of Compt. Rend. Soc. Biol. (1952), 146, 288-90).
Clancey, V. J. (DN 21:13540, HCAPLUS, abstract of Biochem. J. (1926), 20, 1186-9).
Irreverre, et al., (DN 57: 76282, HCAPLUS, abstract of Biochem. Biophysics. Res. Commun. (1962), 8, 453-5).

*Primary Examiner*—Chih-Min Kam
(74) *Attorney, Agent, or Firm*—Knobbe, Martens Olson & Bear LLP.

(57) ABSTRACT

A method for stimulating cell growth includes administrating to a candidate a sponge protein hydrolysate which is a product by acidic hydrolysis of sponge skeleton fibers (spongin fibers) obtained from refined sponges as the raw material. The product has (i) a molecular weight of less than 5,000, with light coloring, and (ii) a human cell growth stimulating activity. The above substances can be used in the form of food product materials, pet food materials, cosmetics or medicinal products to reduce wrinkles and protect the hair cuticles.

7 Claims, 4 Drawing Sheets

METHOD FOR STIMULATING CELL GROWTH USING SPONGE PROTEIN HYDROLYSATES

This is a continuation of U.S. patent application Ser. No. 09/665,848, field Sep. 20, 2000, now abandoned, which claims priority to Japanese Patent Application No. 2000-102424, filed Apr. 4, 2000, the disclosure of which is incorporated herein by reference in its entirety.

BACKGROUND OF THE INVENTION

1. Field of the Invention

The present invention relates to a sponge protein solution for use as food product materials, pet food materials, cosmetics or medicinal products and to provide a growth stimulating effect on cells derived from mammals, which is obtained by dissolving dried sponges and then neutralizing the resultant supernatant.

The present invention further relates to sponge protein hydrolysates which are obtained by hydrolyzing sponge skeleton fibers (spongin fibers) obtained from sponges of Spongia which belongs to Porifera, with light coloring.

2. Description of the Related Art

Until now, attempts have been made to isolate and purify useful proteins from materials which are usually discarded as wastes, such as the blood from slaughtering in the livestock industry, and stick water, waste water concentrates from fish meat soaking water, or canned food broth in the fish processing industry. However, virtually nothing ha been reported about the effective use of proteins from poriferans, which are fibrous sponges.

Poriferans have been conventionally used as sponges for body cleansing or cosmetic use, and are today regularly used as high-quality sponges because these sponges are highly water absorbent and extremely gentle to the skin as compared to other natural and synthetic sponges. But in reality, they are used only for cleansing, cosmetic or the like and not effectively for other purposes. Furthermore, no useful application had been found for the unused shavings from those poriferans used as the abovementioned sponges, and had inevitably been discarded.

Analysis showed that besides water, the fibrous substance used as poriferan sponges are comprised primarily of proteins, and an amino acid analysis showed that the proteins are rich in useful amino acids such as glycine, aspartic acid, glutamic acid, proline and arginine. However, a beneficial use of these poriferan sponges has yet to be found.

Further, in the conventional utilization of poriferans (phylum Porifera), spongin fibers obtained from sponges of family Spongia (order Keratosa, class Demospongea) comprise odorless, soft and highly absorbent spongy structures and have long been used as an absorbent for water, a dusting material for lithographs, a cleansing material for babies or an applicator for cosmetics.

Recently, attention has been drawn to the more value-added use of sponge components, and anti-cancer components, protein adsorbing enzymes or the like have been extracted from sponges. Analysis shows that the spongin fiber component of family Spongia consists of marine proteins rich in amino acids such as glycine, aspartic acid, glutamic acid, proline and arginine, which are effective in human cell growth stimulation when used as cosmetics, medicinal products and food products. However, little is known about the technology for utilizing marine protein hydrolysates derived from sponges in cosmetics, medicinal products, food products or the like.

SUMMARY OF THE INVENTION

In the course of an intensive study on effective uses of poriferans, for example, as a protein hydrolysate having a physiological activity and high palatability, the present inventors found that a protein hydrolysate having a physiological activity and high palatability can be produced by dissolving the proteins contained in fibrous sponges with an alkaline solution, acid solution or protein hydrolases, which led to the present invention. Namely, the present inventors found that a sponge protein solution by itself, which is obtained by dissolving dried sponges and then neutralizing the resulting supernatant, and a sponge protein hydrolysate, which is produced by treating with a protein hydrolase said sponge protein solution obtained by neutralizing the supernatant, have a markedly high physiological activity and palatability and can be used for food product materials, pet food materials, cosmetics or medicinal products and to provide a growth stimulating effect on cells derived from mammals.

Furthermore, the present inventors found that functional low-molecular-weight peptides and/or amino acids which are obtained by further purifying the protein hydrolysate thus obtained using an ultrafiltration membrane, microfiltration membrane, gel filtration or ion-exchange resins, can also, like the protein hydrolysate, be used for food product materials, pet food materials, cosmetics or medicinal products, and to provide a growth stimulating effect on cells derived from mammals.

In a method of producing a sponge protein lysate according to an embodiment of the present invention, a dilute solution of an alkali such as sodium hydroxide, potassium hydroxide, calcium hydroxide and magnesium hydroxide, preferably at a concentration of 0.01 to 50% by weight is added to a material of dried marine sponges, and the admixture is then stirred for sufficient dissolution. Alternatively, a highly concentrated solution of an acid such as hydrochloric acid, sulfuric acid, nitric acid, formic acid and acetic acid, preferably at a concentration of 0.01 to 50% by weight is added to a dried material, and the admixture is then stirred for sufficient dissolution. Heating together with the abovementioned alkalization or acidification can effectively promote the dissolution.

Next, according to an embodiment, the abovementioned dissolved fibrous sponges solution may be neutralized, and the resulting insolubles are removed by centrifugation or with a filter cloth. Then, the filtrate may be treated with activated carbon to remove the abnormal odor and brown color. In this stage, a clear, viscous sponge protein lysate is obtained. For further purification of the protein lysate thus obtained, precipitation by salting-out, for example, with ammonium sulfate, precipitation by organic solvents such as ethyl alcohol, methyl alcohol or acetone, gel filtration treatment, ion-exchange resin treatment, or the like is additionally carried out. It was revealed that the protein lysate derived from sponges thus obtained can be used in various fields as food product materials, pet food materials, cosmetic/medicinal product materials, or the like.

In producing the sponge hydrolysate, it is preferable to reduce the molecular weight of the protein lysate with protein hydrolases since the sponge protein lysate has a high molecular weight, which makes the lysate highly viscous and difficult to handle in higher concentrations. Using the abovementioned sponge protein lysate as a substrate of the protein hydrolase in this decomposition not only solves the problem of handling but the fragmentation of the molecules also provides physiologically active peptides and amino acids having cell stimulating activity or anti-cancer activity.

If proteins extracted from sponges have a high molecular weight, the cell growth stimulating effect on skin or hair is low and only a slight therapeutic effect is expected. Furthermore, these proteins have low moisture-retaining efficacy and cannot protect skin or hair. Therefore, it is preferable to reduce the molecular weight to less than 5,000, which usually requires complicated processes such as hydrolysis using proteases, and purification of an extract may be laborious. According to another embodiment of the present invention, the problem of the coloring of the hydrolysate is solved, and a hydrolysate having a molecular weight of less than 5,000 can be obtained at high yield without using a protein hydrolase.

In the above, the method may use spongin fibers obtained from sponges of Spongia which belongs to Porifera (hereinafter referred to as Spongia sponges), as the raw material. Spongia sponges are preferably refined to remove impurities and soils and then crushed before hydrolysis.

In an embodiment, Spongia sponges are soaked, with heating, in an acidic solution in which the pH is adjusted to 1 using electrolytic acidic water with a pH of less than 2.5 and an oxidation-reduction potential of more than 1,000 mV admixed with an acid to carry out hydrolysis to obtain sponge proteins having a molecular weight of less than 5,000, with light coloring. After the hydrolysis, the hydrolysate may be neutralized using sodium hydroxide and desalted using a reverse osmotic membrane or ion-exchange resins.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

DETAILED DESCRIPTION OF THE PREFERRED EMBODIMENT

Figure 1:
FIG. 1 shows the effect of the control sample on the hair cuticle; it was observed that the cuticle was loosened and thus evidently damaged.

The present invention includes an aspect wherein a sponge protein material is hydrolyzed with proteases and another aspect wherein a sponge protein material is hydrolyzed with a specific acidic solution composed of an acid and an electrolytic acidic water. First, the former aspect will be explained. The term "invention" means an embodiment or an aspect falling within the scope of the present invention including various embodiments and aspects.

In the present invention, the concentration of the substrate, sponge protein lysate, is not particularly restricted, and 0.1 to 15% by weight is generally appropriate. In a successive isolation of the reaction product produced by the hydrolysis reaction using an ultrafiltration membrane or microfiltration membrane as described below, if the protein concentration is higher than 15% by weight, the membrane could get clogged up, and the productivity of the protein lysate will drop. On the other hand, if the protein concentration is lower than 0.1% by weight, the concentration of the reaction product becomes extremely low and an enormous amount of energy and time is required to concentrate the protein lysate.

Protein hydrolases to be used in the present invention are not particularly restricted and generally, protein hydrolases derived from animals, plants or microorganisms are preferably used. Endo-type and exo-type protein hydrolases can be used either alone or in combination in an appropriate ratio depending on the purpose. Further, the protein hydrolases to be used can be dissociated, crosslinked with one another, formed into inclusion compounds, or immobilized onto an insoluble carrier.

Protein hydrolases to be used in the present invention can be immobilized onto an insoluble carrier via covalent bonds, ionic bonds or by physical adsorption. Examples of the insoluble carrier include carboxymethyl cellulose, ethylene-maleic acid co-polymer, carboxychloride resin, carbodiimide resin, acrylamide-methacrylic acid co-polymer, cyanogen bromide-activated polysaccharide, DEAE-cellulose, DEAE-Sephadex, amberlites, activated carbon, porous glass, acid clay, silica gel, alumina, bentonite, polysulfone, polyamide, polyimide, polyether sulfone, cellulose acetate, and polyacrylnitrile.

Protein hydrolases crosslinked with one another can be used. Examples of crosslinking agents include glutaraldehyde, isocyanate derivatives, bis(diazobenzidine), N,N'-polymethylenebis(iodoacetamide), and N,N'-ethylenebis(maleinimide). Further, protein hydrolases can be immobilized through inclusion by confining them into lattices of polymer gel (lattice type), or by coating with a semitransparent polymer coating (microcapsule type). Examples of polymers to be used for the lattice-type immobilization include polyacrylamide gel, polyvinyl alcohol gel, silica gel, starch matrix, and powdered konnyaku. Examples of polymers used for microcapsule-type immobilization include nylon, polyurethane, ethyl cellulose, polystyrene, collodion, cellulose nitrate, butyl cellulose acetate, polyurea, and polyamide.

A sponge protein solution itself, which is obtained by dissolving dried sponges and neutralizing the resulting supernatant using an alkaline solution or acidic solution, can be used for food product materials, pet food materials, cosmetics or medicinal products and to provide a growth stimulating effect on cells derived from mammals.

Furthermore, a protein hydrolysate derived by treating said sponge protein solution with protein hydrolases can be used similar to the sponge protein solution. Protein hydrolases to be used here are not particularly restricted, and can be dissociated, crosslinked with one another, formed into an inclusion compound, or immobilized onto an insoluble carrier. Endo-type and exo-type protein hydrolases can be used either alone or in combination in an appropriate ratio.

As mentioned above, although the sponge protein hydrolysate can be used in food products, cosmetics, medicinal products or the like without further processing, it can be concentrated by an appropriate method if necessary. For example, it can be concentrated by a general method such as evaporation by heating, or easily and effectively by a reverse osmosis method. Furthermore, the hydrolysate can be reduced to a powder, for example, by spray drying after concentrating appropriately as described above.

Further, the hydrolysate can be treated using gel filtration, ion-exchange resins, microfiltration membrane, ultrafiltration membrane, or the like to obtain a specific fraction of the hydrolysate, which can be used for further value-added food products, cosmetics or medicinal products and to provide a growth stimulating effect on cells derived from mammals.

In the above-mentioned aspect, relatively complicated processes of hydrolysis using proteases are required, and purification of an extract may be laborious. Further, a method of hydrolyzing animal proteins by heating under strong alkaline or acidic conditions is known. However, there are some problems in this method, in that the coloring of sponge hydrolysates is intensive and cannot be removed even with activated carbon, that the solids concentration in the lightly colored extract solution can be only 2 to 3% by weight and that the extraction yield is as low as 50% at most. According to another aspect of the present invention, the problem of the coloring of the hydrolysate is solved, and a hydrolysate having a molecular weight of less than 5,000 can be obtained at high yield without using a protein hydrolase.

In this aspect, the method may use spongin fibers obtained from sponges of Spongia which belongs to Porifera (hereinafter referred to as Spongia sponges), as the raw material. Spongia sponges are preferably refined to remove impurities and soils and then crushed before hydrolysis.

In an embodiment, Spongia sponges are soaked, with heating, in an acidic solution in which the pH is adjusted to 1 using electrolytic acidic water with a pH of less than 2.5 and an oxidation-reduction potential of more than 1,000 mV admixed with an acid to carry out hydrolysis to obtain sponge proteins having a molecular weight of less than 5,000, with light coloring. After the hydrolysis, the hydrolysate can be neutralized using sodium hydroxide and desalted using a reverse osmotic membrane or ion-exchange resins.

In the present invention, the electrolytic acidic water to be used can be obtained from the anode chamber during electrolysis with the addition of sodium chloride to water. It contains a high concentration of hydrogen ions and hypochlorous acid and has bleaching and pasteurizing effects. The electrolytic acidic water to be used for the present invention can be obtained using a device such as a Suntron-type MWH-1 (a product of Koshin), Calios (a product of Japan Carlit Co. Ltd.) or Oasysbio (a product of Asahi Glass Engineering Co. Ltd.).

Examples of acids to be used in the present invention include hydrochloric acid, sulfuric acid, nitric acid, oxalic acid, acetic acid, citric acid and malic acid. The pH of the acid solution to be used is adjusted to 1 with the acid and electrolytic acidic water. The amount of the acidic solution to be used can be 25 to 50 times the weight of the Spongia sponges. The sponges are soaked in the acidic solution and heated at 80 to 90 C for 6 to 8 hours to carry out hydrolysis with light coloring.

According to the present invention, the hydrolysis produces sponge proteins having a molecular weight of less than 5,000 and the yield is appropriately 100%. The concentration of sponge proteins in the hydrolysate is 1 to 30% by weight, and coloring is extremely light. The protein component of the hydrolysate is rich in amino acids such as glycine, aspartic acid, glutamic acid and arginine as shown in the results of the analysis in Table 2 below.

A light colored sponge protein hydrolysate according to the present invention can be in the form of a liquid or a spray-dried powder and used in cosmetics, medicinal products and food products. Specifically, they are useful as hair care agents for the protection and treatment of damaged hair and as medicines for external application on skin, such as skin moisture-sustaining agents and anti-inflammatories and antiphlogistics, and are used as internal medicines such as health promoting agents, since they are effective in promoting the growth of human cells.

The present invention will be explained by the following examples but not restricted to these examples.

EXAMPLE 1

Dried fibrous sponges were cut into strips, 900 g of a 20% by weight sodium hydroxide solution were added to 100 g of the strips, and the admixture was stirred at 50 C for 1 hour. After dissolution was confirmed, the lysate was neutralized with a 30% by weight hydrochloric acid solution, and the resultant insoluble residues were removed with a filter cloth to obtain a supernatant. The supernatant was poured into a Buchner funnel containing activated carbon to remove the color and odor of the supernatant. The resultant supernatant could be used without further processing, or after reduction to powder using a spray-dryer, as materials for fortified functional food products or pet foods.

EXAMPLE 2

Dried fibrous sponges were cut into strips, 900 g of a 20% by weight sodium hydroxide solution were added to 100 g of the strips, and the admixture was stirred at 50 C for 1 hour. After dissolution was confirmed, the lysate was neutralized with a 30% by weight hydrochloric acid solution, and the resulting insoluble residues were removed by centrifugation to obtain a supernatant. To 500 g of this supernatant were added 50 g of an activated carbon-acid clay mixture (50%-50%), and the admixture was stirred for 30 minutes and then filtered through a filter paper. Next, for protein purification, the filtrate was fractionated by gel filtration and a protein fraction having a molecular weight of about 50,000 to 1,000,000 was recovered and concentrated using a reverse osmosis membrane.

The resultant concentrate was thinly applied on a PET film using a smoother or the like and then dried to obtain a thin film of the sponge protein.

The thin film thus obtained was usable as an artificial skin for medical use.

EXAMPLE 3

Dried fibrous sponges were cut into strips, 9 kg of a 20% by weight sodium hydroxide solution were added to 1 kg of the strips, and the admixture was stirred at 50 C for 1 hour. After dissolution was confirmed, the lyses was neutralized with a 30% by weight hydrochloric acid solution, and the resultant insoluble residues were removed with a filter cloth to obtain a supernatant. To 10 kg of this supernatant was added 1 kg of activated carbon, and the admixture was stirred for 30 minutes and then filtered through a filter paper.

Next, in order to hydrolyze the sponge protein solution, 500 U each of microorganisms-derived endo-type and exo-type proteases per 1 g by dry weight (dry weight of the protein solution was previously measured) were added and the admixture was reacted at 50 C for 8 hours. The hydrolyzing reaction was periodically confirmed by gel filtration. After completion of the reaction, the resultant solution was desalted using a reverse osmosis membrane and the reaction product was reduced to a powder with a spray-dryer.

The powder thus obtained could be used as a seasoning powder containing low-molecular-weight peptides and amino acids.

EXAMPLE 4

In order to hydrolyze the sponge protein solution obtained in Example 3, an enzyme-releasing-type membrane bioreactor device was constructed. Namely, 1 kg of the sponge protein solution and 1000 U of microorganism-derived endo-type proteases per 1 g by dry weight (dry weight of the solution was previously measured) were placed in a substrate tank. The flow rate was adjusted to 0.10 m/s using a pump and the substrate-enzyme admixed solution in the substrate tank was circulated until the temperature reached 50 C. After the temperature reached the target temperature, the membrane pressure was adjusted to 0.5 kg/cm$^2$ and then using an ultrafiltration membrane (average fractionation molecular weight: 20,000), the reaction product was then recovered successively as the filtrate.

The sponge protein solution obtained as the filtrate was supplied into a substrate tank from a reserve tank, and 500 U of proteases per 1 g by dry weight (the dry weight of the protein solution was previously measured) were added once every 2 hours. After completion of the reaction, the reaction product was desalted using a reverse osmosis membrane and reduced to a powder with a spray-dryer.

Results of its use were shown in Table 1.

EXAMPLE 5

In order to hydrolyze the sponge protein solution obtained in Example 3, proteases were pre-immobilized onto a sponge layer of an ultrafiltration membrane (amount of enzyme immobilization: 50 U/cm$^2$ of membrane area) by the cross-linkage method using glutaraldehyde, and this membrane was used instead of the ultrafiltration membrane of the enzyme-releasing-type membrane bioreactor device used in Example 4. Namely, 1 kg of the sponge protein solution was placed in the substrate tank, the flow rate was adjusted to 0.10 m/s using a pump and the substrate solution in the substrate tank was circulated until the temperature reached 50 C. After the temperature reached the target temperature, the membrane pressure was adjusted to 0.5 kg/cm$^2$ and then using the ultrafiltration membrane (average fractionation molecular weight: 10,000), the reaction product was recovered successively as the filtrate. The sponge protein solution obtained as the filtrate was supplied to the substrate tank from a reserve tank. After completion of the reaction, the resultant filtrate, i.e., the reaction product, was desalted using a reverse osmosis membrane and reduced to a powder with a spray-dryer.

Results of its use were shown in Table 1.

EXAMPLE 6

In order to hydrolyze the sponge protein solution obtained in Example 3, an enzyme-immobilizing-type membrane bioreactor device was constructed. Namely, microorganism-derived endo-type and exo-type proteases were immobilized by an ion-binding method onto ion exchange resins filled in a column (amount of immobilization: endo-type 20 U/cm$^2$ of ion-exchange resin surface area+exo-type 35 U/cm$^2$ of ion-exchange resin surface area). The column temperature was adjusted to 45 C using a heater and the reaction was carried out by supplying the substrate solution to the column from the substrate tank, in which the sponge protein solution was placed, at a flow rate of 10 ml/min.

The sponge protein solution obtained as a reaction product was successively supplied to the substrate tank from a reserve tank. After completion of the reaction, the reaction product was desalted using a reverse osmosis membrane and reduced to a powder with a spray-dryer.

Results of its use were shown in Table 1.

EXAMPLE 7

Dried fibrous sponges were cut into strips, 9 kg of a 20.0% by weight aqueous hydrochloric acid solution were added to 1.0 kg of the strips, and the admixture was stirred at 85 C for 5 hours. After dissolution was confirmed, the lysate was neutralized with a 20.0% by weight sodium hydroxide, and the resultant insoluble residues were removed by centrifugation to obtain a supernatant. To 10 kg of this supernatant was added 1 kg of activated carbon, and the admixture was stirred for 30 minutes and then filtered through a filter paper. Next, for protein purification, the filtrate was fractionated by gel filtration and a protein fraction having a molecular weight of about 5,000 to 500,000 was recovered and concentrated using a reverse osmosis membrane. This concentrate was reduced to a powder with a spray-dryer.

The sponge protein hydrolysate powders obtained in Examples 4 to 7 were each added to a medicinal solution for cosmetic use. As controls, samples without the protein hydrolysate powder (the reduced volume was replaced by ion-exchange water), with collagen, with silk-protein (sericin), and with glycine were similarly prepared to examine the feel when applied on the skin.

Results of their use were shown in Table 1.

TABLE 1

| | | Medicinal solutions for cosmetic use | | | | | | | |
|---|---|---|---|---|---|---|---|---|---|
| No. | Raw material | Cont-1 | Cont-2 | Cont-3 | Cont-4 | Test-1 | Test-2 | Test-3 | Test-4 |
| 1. | 1,3-butylene glycol | 5.0 | 5.0 | 5.0 | 5.0 | 5.0 | 5.0 | 5.0 | 5.0 |
| 2. | Di-propylene glycol | 3.0 | 3.0 | 3.0 | 3.0 | 3.0 | 3.0 | 3.0 | 3.0 |
| 3. | Denatured ethyl alcohol | 10.0 | 10.0 | 10.0 | 10.0 | 10.0 | 10.0 | 10.0 | 10.0 |
| 4. | Cetylpyridium chloride | 0.1 | 0.1 | 0.1 | 0.1 | 0.1 | 0.1 | 0.1 | 0.1 |
| 5. | Allantoin | 0.1 | 0.1 | 0.1 | 0.1 | 0.1 | 0.1 | 0.1 | 0.1 |
| 6. | Ethyl paraoxybenzoate | 0.1 | 0.1 | 0.1 | 0.1 | 0.1 | 0.1 | 0.1 | 0.1 |
| 7. | Citric acid | 0.03 | 0.03 | 0.03 | 0.03 | 0.03 | 0.03 | 0.03 | 0.03 |
| 8. | Sodium citrate | 0.07 | 0.07 | 0.07 | 0.07 | 0.07 | 0.07 | 0.07 | 0.07 |

TABLE 1-continued

| | | Medicinal solutions for cosmetic use | | | | | | | |
|---|---|---|---|---|---|---|---|---|---|
| No. | Raw material | Cont-1 | Cont-2 | Cont-3 | Cont-4 | Test-1 | Test-2 | Test-3 | Test-4 |
| 9. | Ion-exchange water | 81.6 | 81.35 | 81.35 | 81.35 | 81.35 | 81.35 | 81.35 | 81.35 |
| 10. | Hydrolyzed collagen | — | 0.25 | — | — | — | — | — | — |
| 11. | Sericin | — | — | 0.25 | — | — | — | — | — |
| 12. | Glycine | — | — | — | 0.25 | — | — | — | — |
| 13. | Sponge protein hydrolysate (E.-4) | — | — | — | — | 0.25 | — | — | — |
| 14. | Sponge protein hydrolysate (E.-5) | — | — | — | — | — | 0.25 | — | — |
| 15. | Sponge protein hydrolysate (E.-6) | — | — | — | — | — | — | 0.25 | — |
| 16. | Sponge protein hydrolysate (E.-7) | — | — | — | — | — | — | — | 0.25 |
| Feel Evaluation*: | Softness | 3 | 4 | 4.5 | 4 | 3.5 | 4 | 3.5 | 4 |
| | Suppleness | 3 | 4 | 3.5 | 3 | 4 | 3.5 | 4 | 4 |
| | Smoothness | 3 | 3.5 | 3.5 | 3.5 | 3.5 | 4 | 4 | 4 |
| | Slipperiness | 3 | 4 | 4.5 | 4 | 4 | 4 | 4 | 3.5 |
| | Quick fitness | 3.5 | 4 | 4 | 4 | 4.5 | 4 | 4 | 4 |

*Feel Evaluation
5: Very good
4: Good
3: Average
2: Poor
1: Very Poor
Cont: Control preparation.
Test: Test preparation of the present invention Results in Table 1 shows that the sponge protein hydrolysates obtained in Examples 4 to 7 rendered the feel equivalent to that with preparations using proteins and amino acids conventionally used as materials for cosmetics (control samples 1 to 4). Considering economical the cost of the material of the present invention, the benefit is obviously enormous.

EXAMPLE 8

The sponge protein hydrolysate powders obtained Examples 4 to 7 were tested for growth stimulating activity on human epidermal keratinocytes. As control samples, the sponge proteins before the activated-carbon treatment in Examples 4 to 7 and hydrolyzed collagen were used. The protein concentration of each sample was adjusted to 1.0%, calculating the protein content from the amount of nitrogen obtained by the Kjeldahl method. Using a 24-well culture plate, 2.0 ml of F-12 medium (supplemented with hydrocortisone, adenine and fetal calf serum), $2 \times 10^6$/ml epidermal keratinocytes, and the sponge proteins at a final concentration of 0.003125 to 0.1% were incubated at 30 C in an atmosphere of 5.0% $CO_2$ for 7 days. After incubation, the number of viable cells was measured by the change in color of MTT (3-[4,5-dimethylethiazol-2-yl]-2,5-diphenyltetrazolium bromide) (optical density: 570 nm to 650 nm) according to the NTT assay method.

Figure 4:
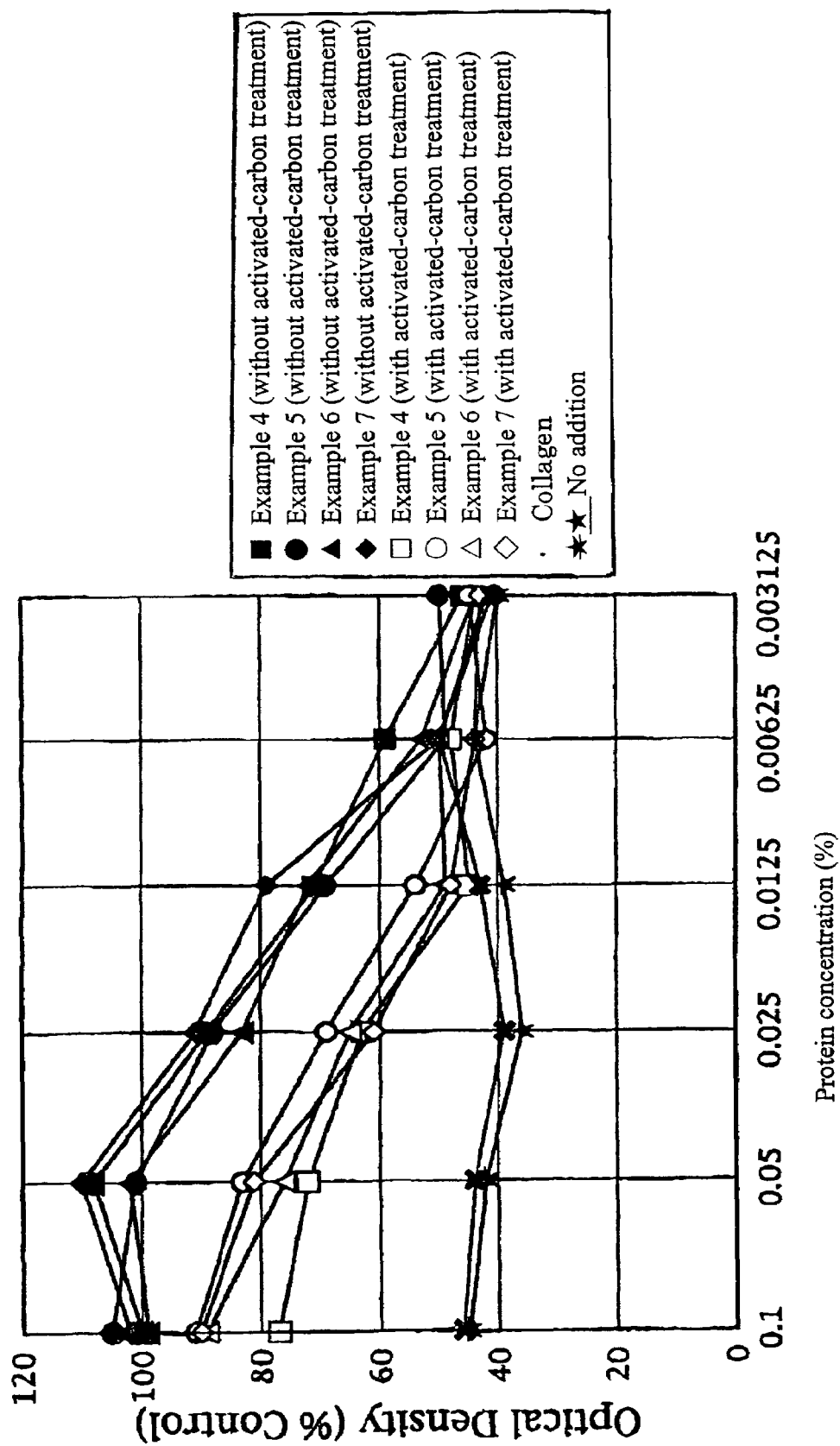
FIG. 4 is a graph showing the relationships between cell growth stimulating effect and concentrations of protein obtained in the Examples.

Results are shown in FIG. 4 (the O.D. value for the sample of Example 4 without the activated-carbon treatment was set to 100%). The sample with collagen showed absolutely no stimulating effect on the growth of epidermal keratinocytes, while the sponge protein showed a cell growth stimulating effect at concentrations of more than 0.00625%.

[Effectiveness of the Invention]
In the above embodiments of the present invention, poriferan sponges which have been conventionally used only as sponges for body cleansing, makeup or the like, and shavings of which have been discarded as wastes, are used as a raw material to obtain sponge protein hydrolysates as a material for value-added food products, pet foods, cosmetics, medicines or the like. This is a perfect fit with social needs.

Furthermore, the sponge protein hydrolysate obtained in the present invention can be purified for use as even more economical raw materials, and thus the social usefulness of this invention should be highly appreciated.

EXAMPLE 9

Acidic water of pH 1 was prepared using electrolytic acidic water produced by a Suntron type MWH-1 and hydrochloric acid. One kg of crushed Spongia sponges were soaked in a 40-fold volume of acidic water and hydrolyzed at 90 C for 7 hours. A light colored material with almost no remaining residue was obtained. After cooling to room temperature, the resultant material was neutralized with a 40% sodium hydroxide solution and filtered. Then, ion-exchange resins (cation and anion mixed type) were added to the filtrate and the admixture was stirred for 2 hours for desalting. The ion-exchange resins were then removed by filtration to obtain a sponge extract solution having 15% by weight of the sponge hydrolysate. After adding 0.1% methylparaben and 10% ethanol as stabilizers, the sponge extract solution was stored at 4 C in a dark place.

The sponge extract solution thus obtained was analyzed by an amino acid analyzer (LC-10AD System, a product of Shimadzu Corp.). Results are shown in Table 2.

A molecular weight distribution for the sponge extract was determined using an Asahipak GS-320 column (column temperature: 40 C; detector: RI, UV 280 nm). An average molecular weight of 4,500 was obtained.

TABLE 2

| Amino acid composition of the sponge extract solution (%) | | | |
|---|---|---|---|
| Hydroxyproline | 8.13 | Valine | 1.71 |
| Aspartic acid | 4.44 | Isoleucine | 1.02 |
| Threonine | 1.98 | Leucine | 1.91 |
| Serine | 1.45 | Tyrosine | 0.14 |
| Glutamic acid | 5.69 | Phenylalanine | 0.57 |
| Proline | 4.09 | Histidine | 0.33 |
| Glycine | 58.66 | Lysine | 1.48 |
| Alanine | 4.34 | Arginine | 4.06 |

EXAMPLE 10

The cell growth stimulating effect of the sponge extract solution obtained in Example 9 on human fibroblasts was measured. Cells used were human skin fibroblasts (NBTRGB Riken Cell Bank). Cells were cultured in an MEM medium (Cat. No. 6110-087 GIBCO BRL) supplemented with fetal bovine serum (FBS; Cat. No. 26140-79 GIBCO BRL) at 37 C under an atmosphere of 5% $CO_2$. For the measurement, human skin fibroblasts were suspended in an MEM medium supplemented with 5% FBS, inoculated onto a 96-well microplate at a concentration of $5 \times 10^5$ cells/dish and incubated for 24 hours. Then, the medium was changed to a 0.5% MEM medium, and samples were added. Incubation was continued for 9 days and cells in the dishes were counted by a dye-exclusion method using trypan blue to obtain a cell survival rate.

Results are shown in Table 3.

It was revealed that the sponge extract solution obtained had an excellent cell growth stimulating effect.

TABLE 3

Cell growth stimulating effect of the sponge extract solution

| Amount of sponge extract solution added | Cell survival rate (%) |
|---|---|
| 2.5 | 122 |
| 5.0 | 157 |
| 10.0 | 174 |

EXAMPLE 11

The effect of the sponge extract solution obtained in Example 9 on wrinkles on the outer corner of the eye (crow's feet) was measured. A 1% by weight sponge extract solution was prepared using purified water. A 1% by weight collagen hydrolysate solution was prepared for use as a control.

To each test subject, the sponge extract was applied on the left outer corner of the eye and the collagen hydrolysate was applied on the right outer corner of the eye 2 times a day for 3 weeks. The image of wrinkles was photographed using a video microscope by lighting the skin at a 25-degree angle according to a replica method. Results of image processing analysis are shown in Table 4.

It was revealed that the sponge extract solution was effective to reduce wrinkles.

TABLE 4

Effect of sponge extract solution on skin wrinkles

| | | K (37 years old) Sponge Control | | S (40 years old) Sponge Control | | H (36 years old) Sponge Control | |
|---|---|---|---|---|---|---|---|
| Measurement | Application | Left | Right | Left | Right | Left | Right |
| Depth of wrinkles (μm) | Before | 417 | 240 | 224 | 346 | 456 | 371 |
| | After | 176 | 165 | 162 | 298 | 183 | 248 |
| Area ratio of Wrinkles | Before | 10.7 | 6.5 | 9.8 | 10.6 | 8.2 | 7.8 |
| | After | 5.4 | 4.9 | 6.0 | 9.4 | 5.4 | 6.9 |

EXAMPLE 12

The effect of the sponge extract solution obtained in Example 9 on the hair cuticle (cuticula pili) was studied.

Sponge extract solution: a 1% by weight sponge extract solution was prepared using purified water.

Control: a 10% ethanol solution containing 0.1% methylparaben was used as a control.

Hydrolyzed collagen: a 1% hydrolyzed collagen was used as a reference.

In each test, a 10 cm hair strands were sampled and made into a bundle and briefly washed with water. Each sample solution was applied to the bundle and allowed to stick onto the hair, and then the bundle was treated with a bleaching agent containing 4% hydrogen peroxide, rinsed with warm water and dried.

After the abovementioned treatment, the surface of the hair samples was observed by scanning electron microscopy.

Figure 2:
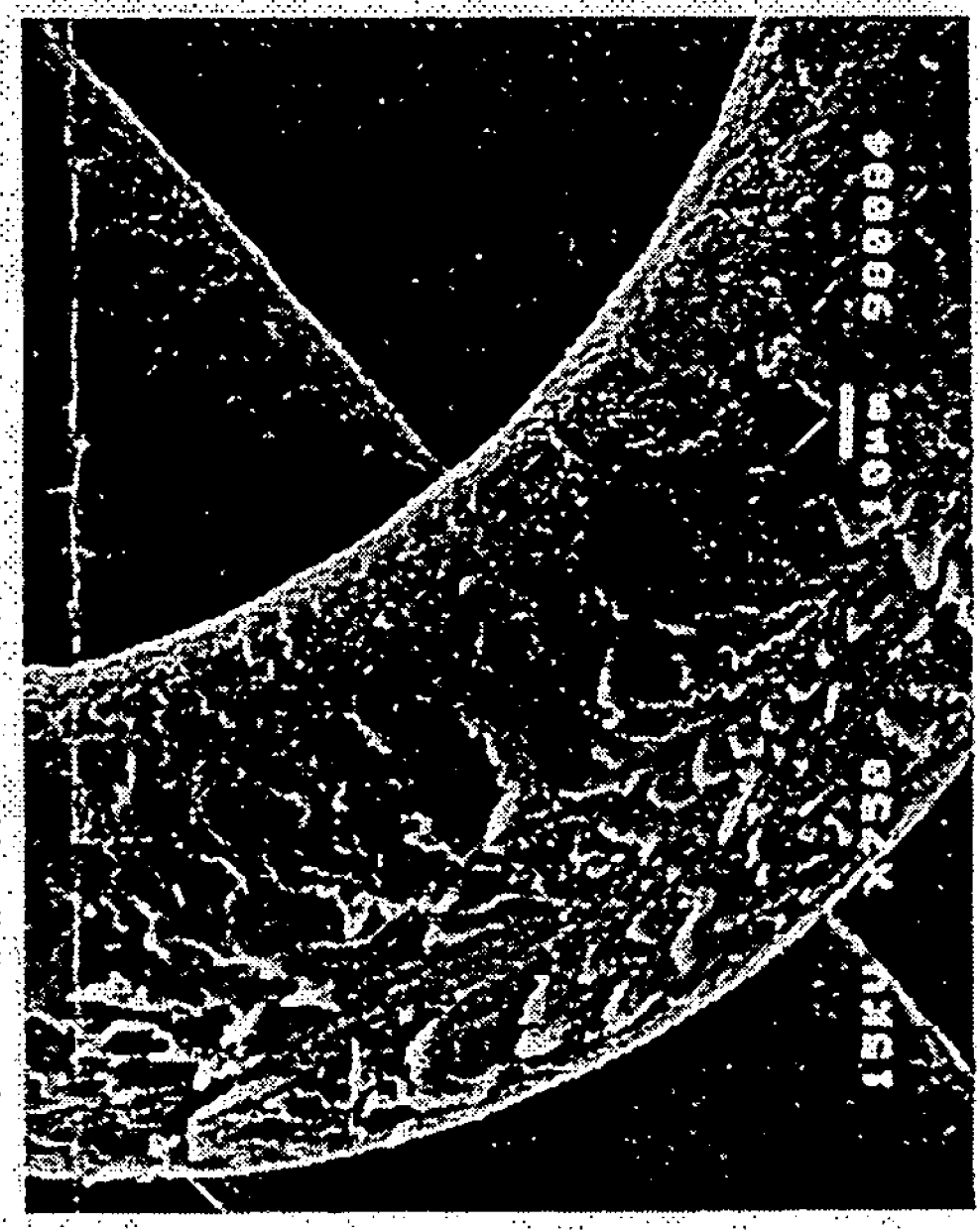
FIG. 2 shows the effect of the sponge extract solution of the present invention on the hair cuticle; no damage to the cuticle was observed, which confirmed that the sponge extract solution suppressed the damage caused by the bleaching agent.
Figure 3:
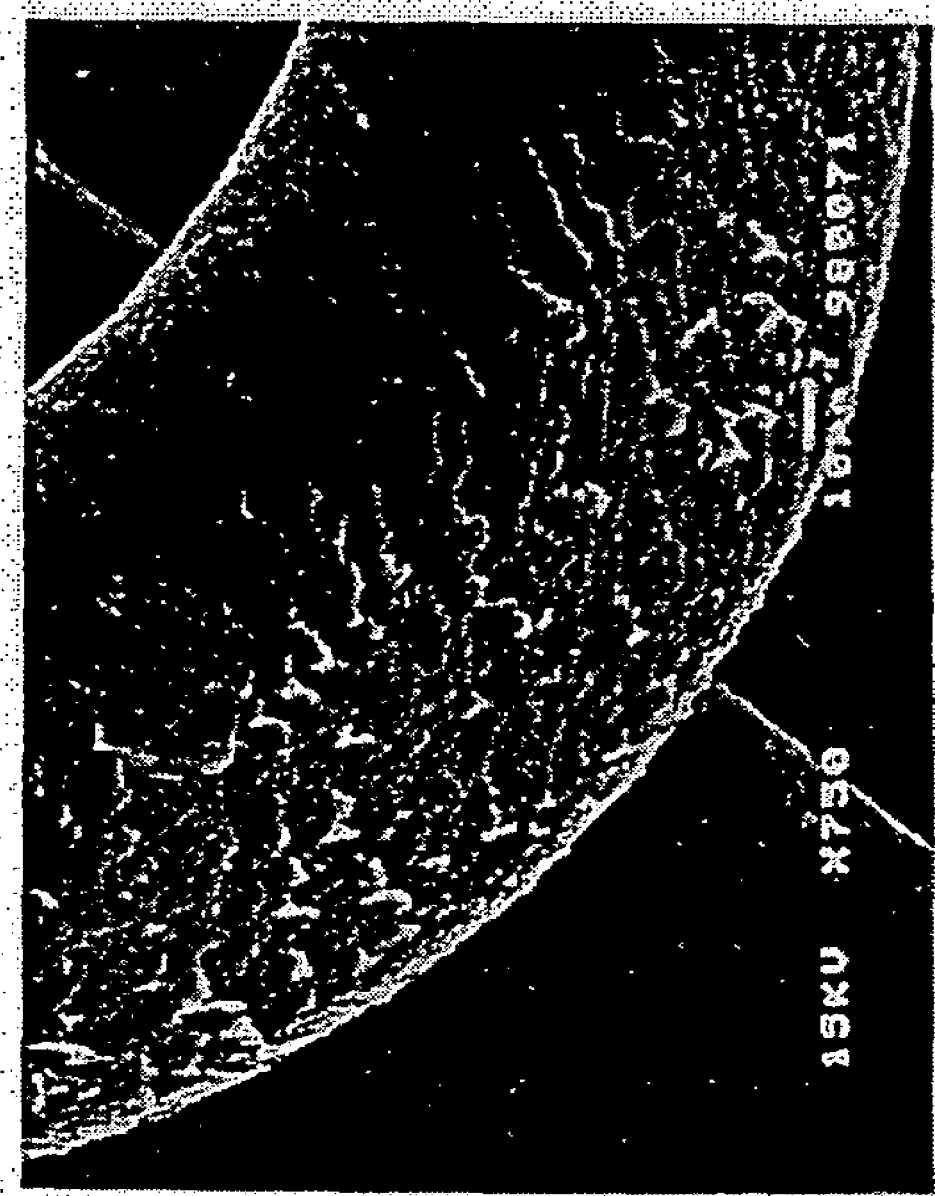
FIG. 3 shows the effect of the reference sample, hydrolyzed collagen, on the hair cuticle; damage to the cuticle was observed.

FIGS. 1-3 are photographs showing the hair surfaces. FIG. 1 shows the effect of the control sample on the hair cuticle; wherein the control solvent was applied on the hair and then which hair was treated with the bleaching agent; it was observed that the cuticle was loosened and thus evidently damaged. FIG. 2 shows the effect of the sponge extract solution of the present invention on the hair cuticle; no damage to the cuticle was observed, which confirmed that the sponge extract solution suppressed any damage caused by the bleaching agent. FIG. 3 shows the effect of the reference sample, hydrolyzed collagen, on the hair cuticle; damage to the cuticle was observed.

[Effectiveness of the Invention]

If proteins extracted from sponges have a high molecular weight, their cell growth stimulating effect on skin or hair is low, and they have little therapeutic effect and low moisture-retaining effect, and thus cannot protect skin or hair. Therefore, it is preferable to reduce the molecular weight to less than 5,000, which usually requires complicated processes such as hydrolysis using proteases, and purification of an extract may be laborious. According to the above aspect of the present invention, the problem of coloring of the hydrolysate is solved and a hydrolysate having a molecular weight of less than 5,000 can be obtained at high yield without using protein hydrolase. The light colored sponge protein hydrolysate obtained in the present invention can be used as a raw material having a human cell growth stimulating effect in cosmetics, medicinal products or food products.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for reducing wrinkles on skins of a human, comprising:
   applying to the skin of the human a sponge protein hydrolysate which is a product by acidic hydrolysis of sponge skeleton fibers (spongin fibers) obtained from refined poriferan sponges as the raw material without using a protein hydrolase, in an amount effective to reduce wrinkles on the skin, said product having (i) a molecular weight of less than 5,000, with light coloring, and (ii) a human cell growth stimulating activity on human fibroblasts.

2. The method according to claim 1, wherein the sponge protein hydrolysate is a sponge protein hydrolysate solution.

3. The method according to claim 2, wherein the sponge protein solution has a concentration of about 0.01% to about 15% by weight.

4. The method according to claim 2, wherein the solution has a concentration of about 0.1% to 15% by weight.

5. The method according to claim 1, wherein the sponge protein hydrolysate is administrated in the form of cosmetics.

6. The method according to claim 1, wherein the acidic hydrolysis is carried out with heat in an acidic solution in which the pH is adjusted to 1 using electrolytic acidic water with a pH of less than 2.5 and an oxidation-reduction potential of more than 1,000 mV admixed with an acid.

7. The method according to claim 6, wherein the sponge protein hydrolysate is a lightly colored solution having a concentration of 1 to 30% by weight.

* * * * *